(12) United States Patent
Garden et al.

(10) Patent No.: US 7,625,375 B2
(45) Date of Patent: Dec. 1, 2009

(54) SYSTEMS AND TECHNIQUES FOR STABILIZING THE SPINE AND PLACING STABILIZATION SYSTEMS

(75) Inventors: Benjamin Garden, Crodova, TN (US); Dusty Anna Needham, Eads, TN (US)

(73) Assignee: Warsaw Orthopedic, Inc.

( * ) Notice: Subject to any disclaimer, the term of this patent is extended or adjusted under 35 U.S.C. 154(b) by 806 days.

(21) Appl. No.: 10/635,319

(22) Filed: Aug. 6, 2003

(65) Prior Publication Data
US 2005/0033294 A1 Feb. 10, 2005

(51) Int. Cl.
*A61F 5/00* (2006.01)
(52) U.S. Cl. .................................................... 606/86 B
(58) Field of Classification Search ................... 606/61, 606/69–71, 246, 275, 280–299, 96–99, 86 A, 606/86 B, 915, 104, 101; 29/432; 408/72 R
See application file for complete search history.

(56) References Cited

U.S. PATENT DOCUMENTS

| | | | | |
|---|---|---|---|---|
| 2,248,054 | A * | 7/1941 | Becker | 81/457 |
| 3,160,188 | A * | 12/1964 | Frank | 411/103 |
| 3,289,290 | A * | 12/1966 | Sandor | 29/432 |
| 4,119,092 | A * | 10/1978 | Gil | 606/96 |
| 4,740,117 | A * | 4/1988 | Deleury et al. | 408/72 R |
| 5,129,906 | A * | 7/1992 | Ross et al. | 606/77 |
| 5,423,826 | A | 6/1995 | Coates et al. | |
| 5,669,915 | A * | 9/1997 | Caspar et al. | 606/96 |
| 5,676,666 | A | 10/1997 | Oxland et al. | |
| 5,755,721 | A | 5/1998 | Hearn | |
| 5,851,207 | A | 12/1998 | Cesarone | |
| 6,066,142 | A | 5/2000 | Serbousek et al. | |
| 6,193,721 | B1 * | 2/2001 | Michelson | 606/70 |
| 6,235,034 | B1 | 5/2001 | Bray | |
| 6,332,887 | B1 | 12/2001 | Knox | |
| 6,342,056 | B1 | 1/2002 | Mac-Thiong et al. | |
| 6,342,057 | B1 | 1/2002 | Brace et al. | |
| 6,379,364 | B1 | 4/2002 | Brace et al. | |
| 6,416,518 | B1 | 7/2002 | DeMayo | |

(Continued)

FOREIGN PATENT DOCUMENTS

EP 0 460 447 A1 5/1991

(Continued)

OTHER PUBLICATIONS

Thomas A. Zdeblick, M.D. and Harry N. Herkowitz, M.D.; Premier Anterior Cervical Plate System, Surgical Technique; Premier Anterior Cervical Plate System; 2000 Medtronic Sofamor Danek.

(Continued)

*Primary Examiner*—Thomas C Barrett
*Assistant Examiner*—James L Swiger

(57) ABSTRACT

Systems for stabilizing the spine and facilitating placement of stabilization devices on the spine include one or more holding elements positionable in corresponding ones of one or more cannulated auxiliary elements of the stabilization device. The holding elements can be configured to manipulate and/or maintain alignment of the corresponding auxiliary element relative to the stabilization device. A driving tool engaged to the holding element facilitates remote manipulation. The systems can further be provided with blocking members engageable to the cannulated auxiliary elements to enhance engagement of the stabilization device with the spine and to facilitate revision surgery.

28 Claims, 13 Drawing Sheets

U.S. PATENT DOCUMENTS

| | | |
|---|---|---|
| 6,436,103 B1 | 8/2002 | Suddaby |
| 7,001,389 B1 * | 2/2006 | Navarro et al. ............... 606/71 |
| 7,063,702 B2 * | 6/2006 | Michelson ................ 606/307 |
| 7,175,624 B2 * | 2/2007 | Konieczynski et al. ........ 606/71 |
| 2001/0047172 A1 | 11/2001 | Foley et al. |
| 2003/0083749 A1 * | 5/2003 | Kuslich et al. ........... 623/17.16 |
| 2004/0019353 A1 * | 1/2004 | Freid et al. .................. 606/69 |

FOREIGN PATENT DOCUMENTS

| | | |
|---|---|---|
| EP | 1 306 058 A1 | 5/2003 |
| FR | 2 822 674 A1 | 10/2002 |
| WO | WO 98/51226 | 11/1998 |
| WO | WO 02/080819 | 10/2002 |
| WO | WO 03/037216 | 5/2003 |

OTHER PUBLICATIONS

Zephir Anterior Cervical Plate System, Surgical Technique; 2000 Medtronic Sofamor Danek; pp. 1-8.

Gary L. Lowery, MD, PhD; Sugical Technique; Orion Anterior Cervical Plate System; Sofamor Danek The Spine Specialist; pp. 1-24.

Trinica™ Anterior Cervical Plate System; 2001, Sulzer Medica Sulzer Spine-Tech.

* cited by examiner

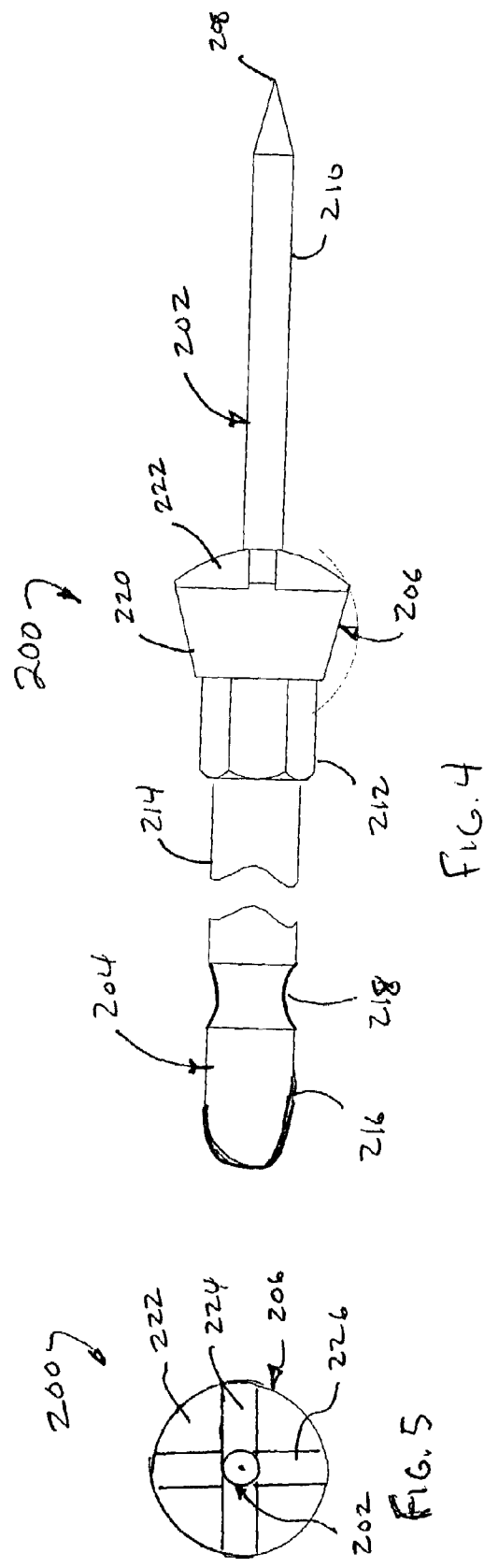

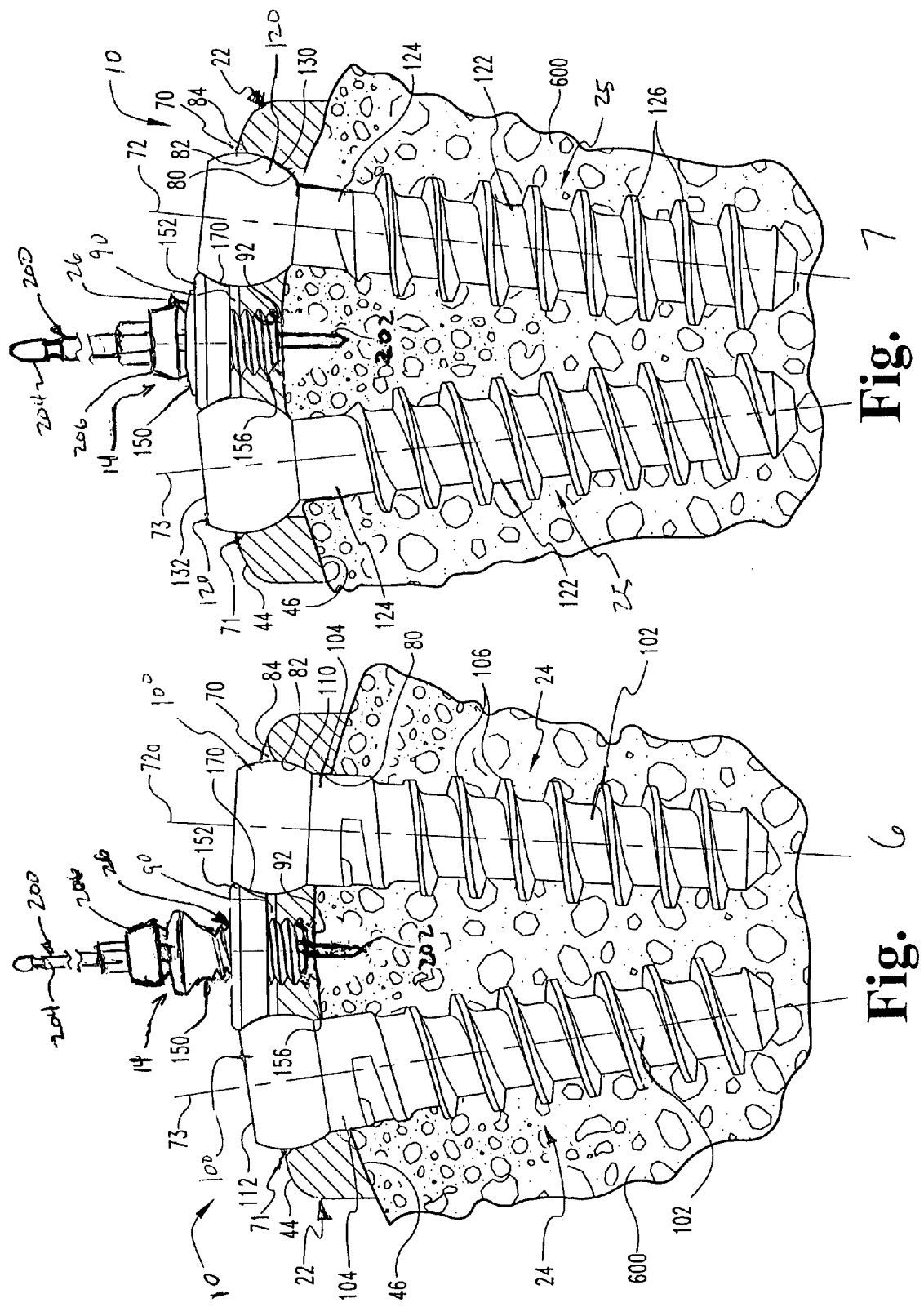

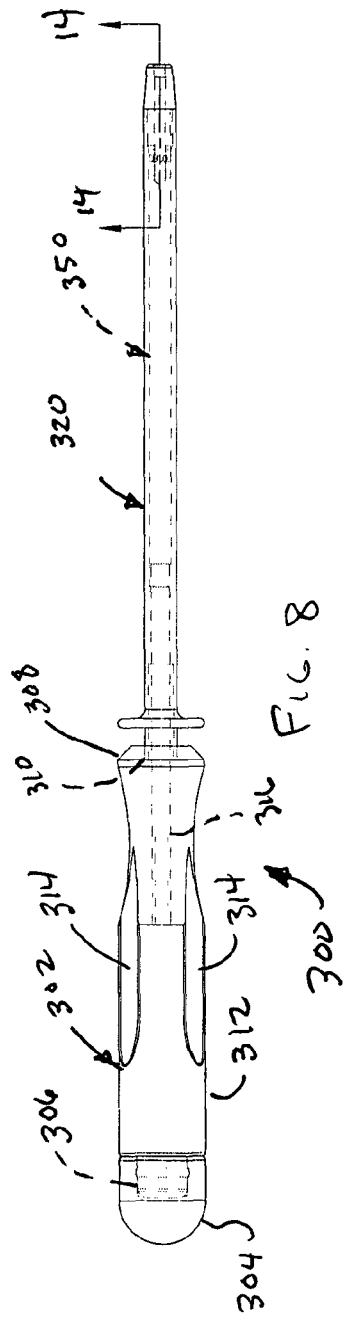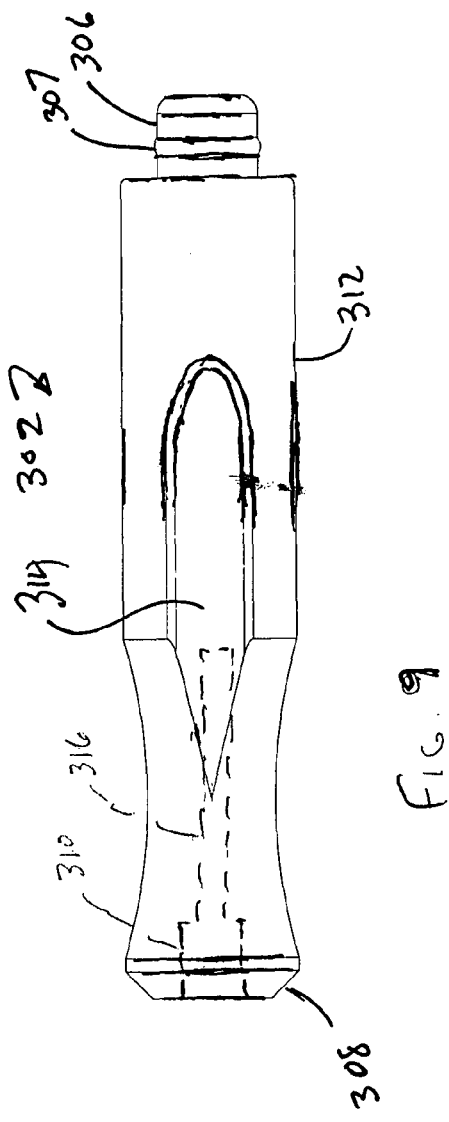

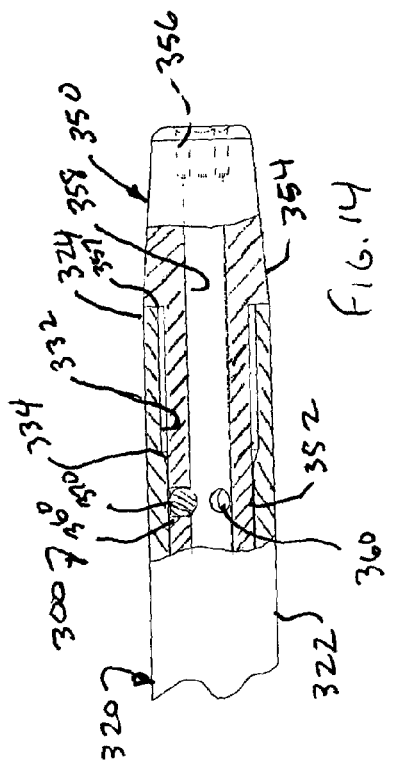
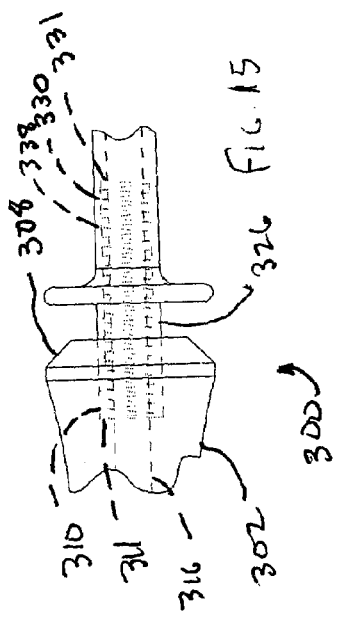
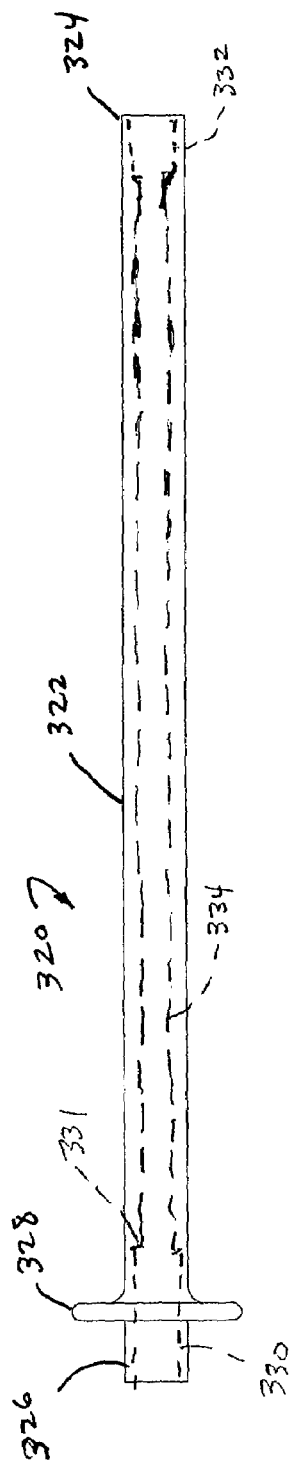

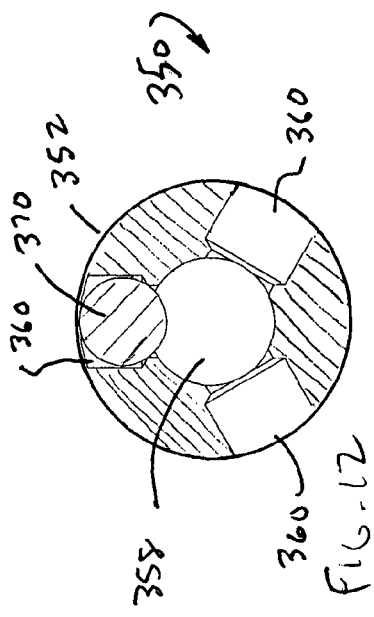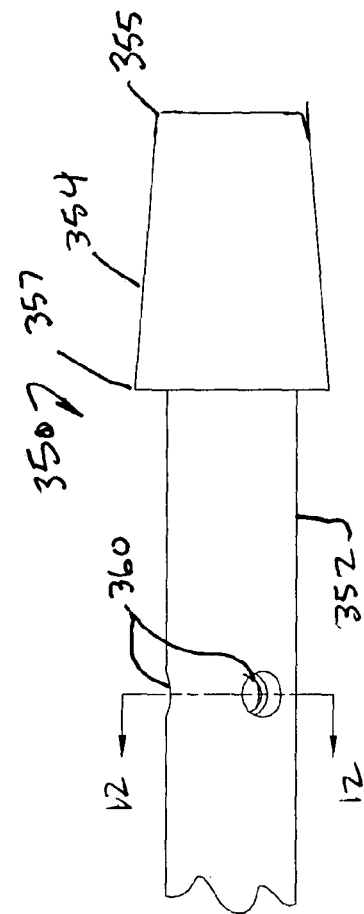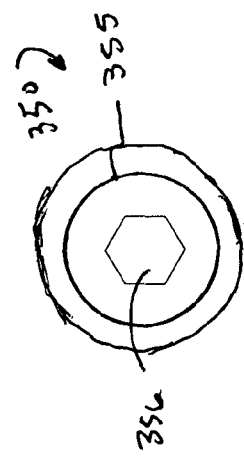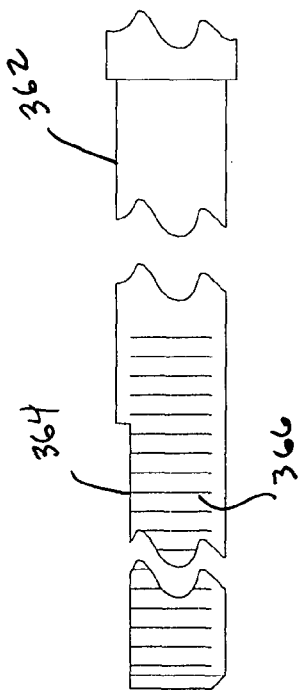

SYSTEMS AND TECHNIQUES FOR STABILIZING THE SPINE AND PLACING STABILIZATION SYSTEMS

BACKGROUND

The invention generally relates to systems for treatment of the spine, and more particularly to systems for placement of stabilization devices on the spine.

It is desirable to maintain the positioning of a stabilization device, such as a plate, before and during attachment of it to the spine. Instruments have been provided to grasp the stabilization device so that it can be remotely held in the desired position during attachment. However, such instruments can obstruct access to the stabilization device, while also occupying space in the surgical site and/or in the approach to the surgical site, hindering attachment of the device to the spine.

Elongated spinal plates have been temporarily secured to the spine with a bone screw positioned through one or more bone screw openings in the plate. This technique, however, requires additional steps since the temporary screw must be removed from the plate for placement of the final bone screw at the proper angle and depth through the plate. Also, the temporary screw limits the order of placement of bone screws through the plate openings. Still further, the temporary screw creates a bore in the bone underlying the plate opening that may not be oriented at the desired angle relative to the plate, making it more difficult to create a bore at the desired angle and/or hindering or preventing the placement of self-drilling or self-tapping screws.

Other elongated plates include holes in addition to the bone screw openings to receive temporary fixation devices therethrough to temporarily secure the plate to the spine. However, these additional holes through the plate provide areas of reduced plate strength, or require the plate size to be increased to compensate for the loss of strength. Still further, these extra holes increase the "fiddle factor" since additional steps are required for placement and removal of temporary fixation devices in these holes in addition to those steps normally required to finally secure the plate to the spine.

Elongated plates can also include devices that prevent bone screws from backing out relative to the plate after it is secured to the spine. The difficulty of revision surgery can be increased when tissue or other bioactivity blocks and/or impedes access to these devices and the bones screws extending through the plate.

Thus, there is a need to provide improved systems and techniques for attaching stabilization devices to the spine and for facilitating revision surgery.

SUMMARY

According to one aspect, a stabilization system includes a stabilization device and an auxiliary element associated with the stabilization device. A holding element includes a distal portion cooperative with the auxiliary element to maintain a position of the stabilization device along the spine column for engagement thereto.

According to another aspect, a holding element includes a proximal portion, a distal portion, and an intermediate portion therebetween. The intermediate portion includes a distally oriented auxiliary element engaging surface adapted engage an auxiliary element.

According to another aspect, a holding element includes a proximal portion, a distal portion, and an intermediate portion therebetween. The proximal portion includes a first tool engaging portion adjacent the intermediate portion and a second tool engaging portion adjacent a proximal end of the holding element. One of the first and second tool engaging portions is adapted to deliver a rotational force to the holding element and the other of the first and second tool engaging portions is adapted to axially secure the holding element to a driving tool.

According to another aspect, a driving tool includes a handle portion and first and second member extending distally from the handle portion. The first member is movable relative to the second member between a first position allowing insertion of a holding element into a distal opening of the second member and a second position that biases a coupling device into engagement with the holding element positioned in the second member.

According to another aspect, a surgical method includes placing a stabilization device along the spinal column and positioning a holding element through a cannulated auxiliary element associated with the stabilization device into engagement with spinal column.

According to another aspect, a surgical method includes placing a stabilization device along the spinal column; positioning a holding element through a cannulated auxiliary element associated with the stabilization device into engagement with spinal column; and remotely manipulating the auxiliary element with a driving tool coupled to the holding element.

According to another aspect, a surgical method includes placing a stabilization device along the spinal column; positioning a holding element through a cannulated auxiliary element associated with the stabilization device into engagement with spinal column; and maintaining an alignment of the auxiliary element relative to the stabilization device with the holding element as the stabilization device is anchored to the spinal column.

According to another aspect, a surgical method includes placing a stabilization device along the spinal column and engaging a blocking member with a cannulated auxiliary element associated with the stabilization device to at least partially cover the auxiliary element and bone anchors of the stabilization device.

According to another aspect, a surgical method includes placing at least two stabilization systems along the spinal column and positioning a holding element through aligned cannulations of the stabilization systems to temporarily align and secure the stabilization systems to the spinal column in a desired relative position to one another.

Further objects, features, advantages, benefits, and further aspects of the present invention will be apparent from the drawings and description contained herein.

BRIEF DESCRIPTION OF THE FIGURES

FIG. 4 is an elevation view of one embodiment of a holding element.

FIG. 5 is a right end view of the holding element of FIG. 4.

FIG. 6 is a partial cross-sectional view of the spinal stabilization system shown in FIG. 1, as secured to a vertebra using the holding element of FIG. 4.

FIG. 7 is a partial cross-sectional view of the spinal stabilization system shown in FIG. 1, as secured to a vertebra using the holding element of FIG. 4 to finally position the auxiliary element on the stabilization device.

FIG. 8 is an elevation view of a driver instrument.

FIG. 9 is an elevation view of a handle comprising a portion of the driving instrument of FIG. 8.

FIG. 10 is an elevation view of a first member comprising a portion of the driving instrument of FIG. 8.

FIG. 11 is an elevation view of a second member comprising a portion of the driving instrument of FIG. 8.

FIG. 12 is a cross-sectional view of the second member of FIG. 11 through line 12-12 thereof.

FIG. 13 is a right end view of the second member of FIG. 11.

FIG. 14 is an enlarged view in partial section of the distal portion of the driving instrument of FIG. 8.

FIG. 15 is an enlarged view of a portion of the driving instrument of FIG. 8 showing the engagement of the first and second members to the handle.

DESCRIPTION OF THE ILLUSTRATED EMBODIMENTS

Figure 1:
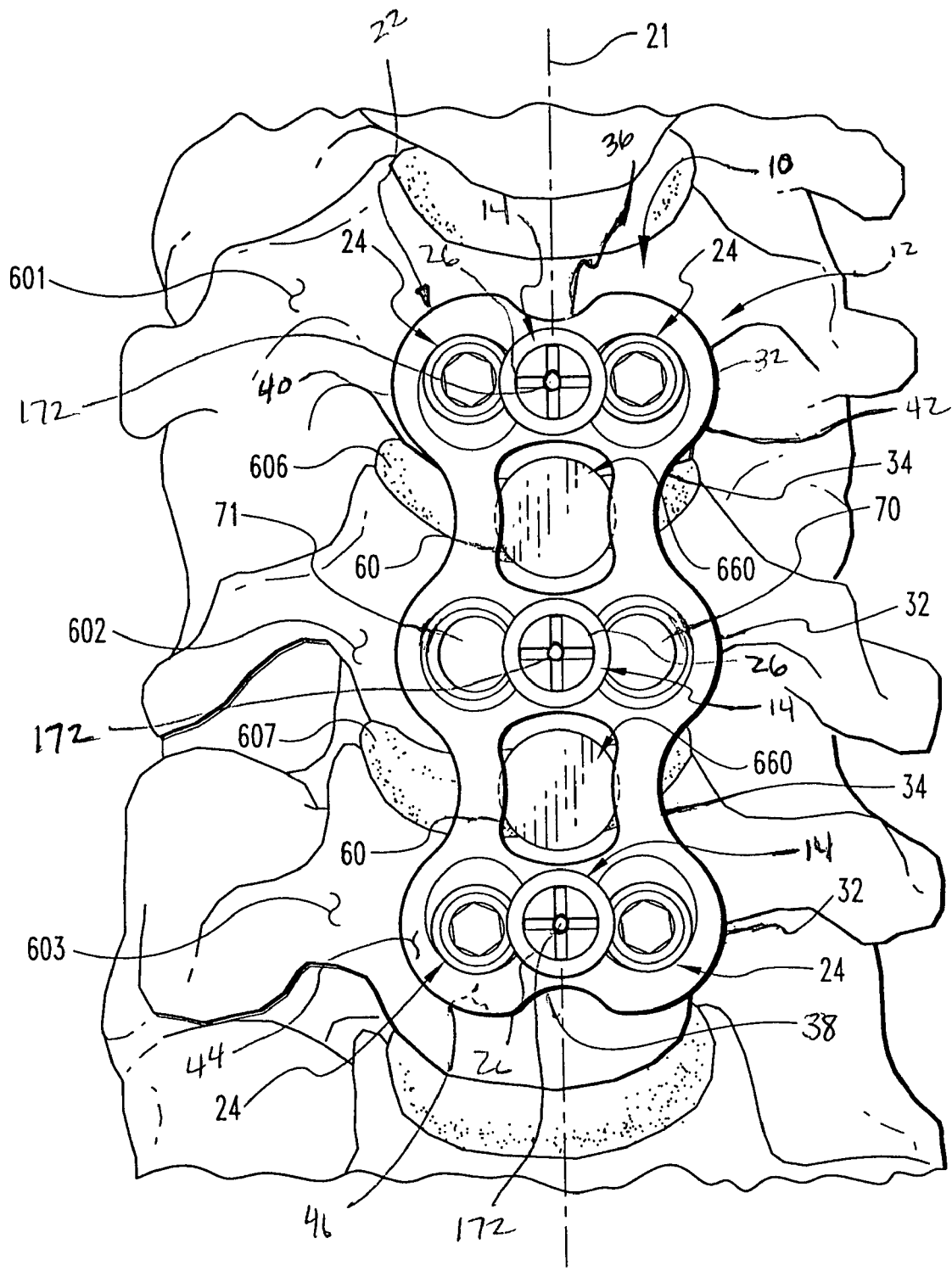
FIG. 1 is a plan view of a spinal stabilization system.

For the purposes of promoting an understanding of the principles of the invention, reference will now be made to the embodiments illustrated in the drawings and specific language will be used to describe the same. It will nevertheless be understood that no limitation of the scope of the invention is hereby intended, such alterations and further modifications in the illustrated devices, and such further applications of the principles of the invention as illustrated herein being contemplated as would normally occur to one skilled in the art to which the invention relates.

Figure 2:
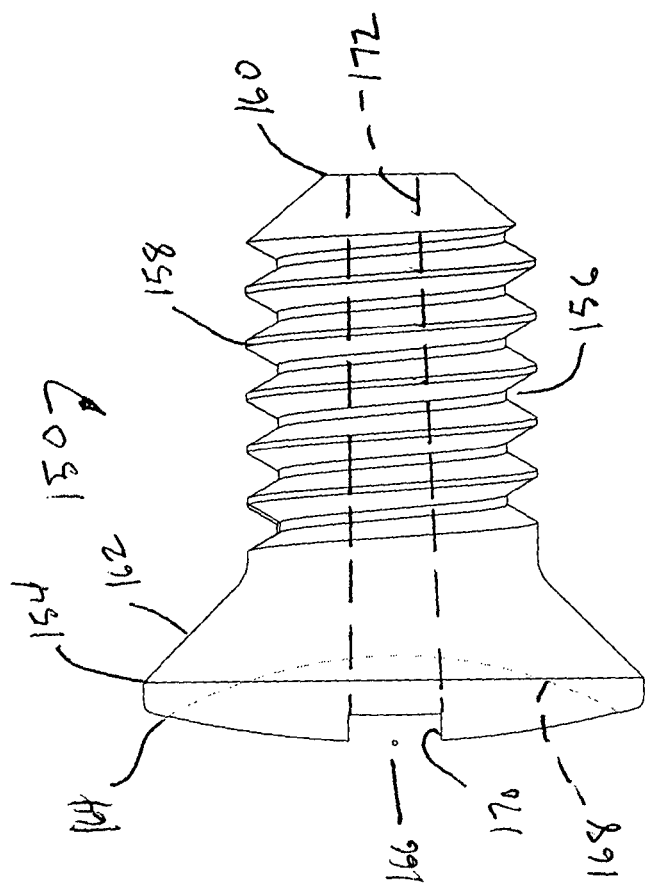
FIG. 2 is an elevation view of a portion of an embodiment of an auxiliary element of the stabilization system of FIG. 1.

Referring to FIGS. 1 and 2, shown therein is a spinal stabilization system 10 for use in stabilizing at least a portion of the spinal column. Stabilization system 10 is generally comprised of a stabilization device 12 and one or more auxiliary elements 14. Stabilization device 12 is attached to the spinal column to, for example, statically and/or dynamically maintain a desired spatial relationship between one or more elements of the spinal column, such as the vertebrae. Auxiliary elements 14 comprise a portion of stabilization device 12, and can be removable or non-removable relative to stabilization device 12. Auxiliary elements 14 can also be movable relative to stabilization device 12, or non-movable relative thereto. In one embodiment, for example, auxiliary elements 14 facilitate, enhance, supplement, support and/or provide primary securement of stabilization device 12 to the spinal column.

Auxiliary elements 14 include a cannulation 172 that opens proximally and extends at least partially through auxiliary element 14. A holding element 200, such as shown in FIGS. 4 and 5, can be positioned into cannulation 172 to facilitate securement of stabilization device 12 to the spinal column. In one embodiment, holding element 200 includes a distal portion 202, a proximal portion 204, and an intermediate portion 206. In one embodiment, distal portion 202 is positionable through cannulation 172 to engage the spinal column with proximal portion 204 extending proximally from auxiliary element 14 for access. In another embodiment, distal portion 202 engages auxiliary element 214 without extending completely therethrough for remote manipulation and holding of stabilization device 10 at the desired position on the spinal column. Intermediate portion 206 resides adjacent auxiliary element 14, and can be configured to engage auxiliary element 14 to facilitate manipulation and/or movement of auxiliary element 14, although such is not required.

In embodiments where distal portion 202 of holding element 200 extends completely through cannulation 172, distal portion 202 can engage any portion of the spinal column, including bony tissue of an underlying vertebral body, soft tissue of a disc or other soft tissue structure, or an implant positioned in a disc space or between vertebrae in a corpectomy procedure. Holding element 200 can be readily engaged to the spinal column through auxiliary element 14 to provide securement of stabilization device 12 to the spinal column to facilitate subsequent surgical procedures while minimizing obstruction of the surgical space and of stabilization device 12. In other embodiments, distal portion 202 of holding element 200 engages auxiliary element 14 in cannulation 172 and, with auxiliary element 14 attached to stabilization device 12, holding element 200 can be used to position the stabilization device 12 along the spinal column and held in position manually or with a tool engaged to proximal portion 204.

In the illustrated embodiment of FIG. 1, stabilization device 12 includes a plate 22 extending along a longitudinal axis 21 and configured for anterior attachment to the spinal column. However, it should be understood that stabilization device 12 can include one or more plates, rods, tethers, braces, or other devices that may be utilized in other areas of the spinal column, such as the thoracic, lumbar, lumbo-sacral and sacral regions of the spinal column. It should also be understood that stabilization device 12 can extend across any number of vertebrae, including a pair of adjacent vertebrae or three or more vertebrae. Additionally, although plate 22 has application in an anterior surgical approach to the spinal column, stabilization system 10 can employ stabilization devices 12 in other surgical approaches, such as, for example, antero-lateral, lateral, oblique and posterior surgical approaches to the spinal column. In one embodiment, plate 22 is formed of a metallic material such as, for example, stainless steel or titanium. However, it should be understood that plate 22 may be formed from any one or combination of a number of materials including, for example, a pure metallic composition, a metallic alloy, a shape-memory alloy, a polymer material, a synthetic material, a biologic material, and/or a resorbable material, and combinations thereof.

In one embodiment, bone anchors 24 are configured as bone screws. However, other types of bone anchors are also contemplated, such as, for example, bolts, hooks, staples, cables, or other types of devices suitable for attaching plate 22 to vertebrae 601, 602, 603. Auxiliary elements 14 include a number of retaining devices 26 adapted to engage or overlap openings in the plate 22 that receive bone anchors 24, and function to prevent or limit bone anchors 24 from loosening and backing out of plate 22. Retaining devices 26 engage adjacent pairs of bone anchors 24 to prevent the bone anchors 24 from loosening and/or backing out. In the illustrated embodiment, retaining devices 26 each include a retaining fastener 150 that engages plate 22 and a retaining member 152, such as a washer, that receives fastener 150 therethrough and abuts against the heads of adjacent bone anchors 24. However, other types of retaining devices 26 are contemplated including, for example, pop rivets, retainers, a blocking plate that substantially covers the heads of the adjacent bone anchors, a lock washer or plate rotatably displaceable between an unlocked position and a locked position, a retaining device integrally formed with the plate, a retaining fastener integrally formed with a retaining member, or any other type of retaining element, device, mechanism or system. The retaining devices can be positioned on the plate to retain a single bone anchor or multiple bone anchors.

Plate 22 includes multiple nodes or connection portions 32 that are configured to receive a pair of bone anchors 24 to anchor plate 22 at each vertebral level. The connection portions 32 are separated from one another by intermediate portions 34. Plate 22 has opposite end surfaces 36, 38, opposite side surfaces 40, 42, and opposite upper and lower surfaces 44, 46. The corners of plate 22 between end surfaces 36, 38 and side surfaces 40, 42 can be rounded to eliminate sharp or abrupt edges that could pinch, cut or wear against tissue. The corners of plate 22 between upper surface 44 and the end and side surfaces 36, 38, 40 and 42 can also be rounded to eliminate sharp or abrupt edges that could pinch, cut or wear against tissue.

When plate 22 is attached to the spinal column, lower surface 46 abuts an outer vertebral surface. In one embodiment, lower surface 46 of plate 22 defines a concave lateral curvature which corresponds to the anatomical lateral curvature of the vertebrae 601, 602, 603. Lower Surface 46 may also define a concave curvature extending along longitudinal axis 21 which corresponds to the normal lordotic curvature of vertebrae 601, 602, 603. In one embodiment, upper surface 44 of plate 22 defines a convex curvature that substantially corresponds to the concave curvature(s) of lower surface 46 to reduce the amount of trauma to the adjacent soft tissue when plate 22 is secured to the vertebrae and to reduce the overall profile of plate 22. It should be understood, however, that plate 22 can take on other configurations to accommodate the specific spinal anatomy and pathology involved in the particular application of stabilization system 10.

In one embodiment, side surfaces 40, 42 have a serpentine shape or corrugated configuration so as to form an undulating curve or sinusoidal pattern extending along longitudinal axis 21. It should be understood, however, that side surfaces 40, 42 can take on other shapes and configurations, such as, for example, triangular or rectangular shape so as to define a zigzag or tooth-like configuration, linear configurations, and inwardly or outwardly bowed or arched configurations.

In one embodiment, plate 22 includes a number of visualization openings or windows 60 extending through intermediate portions 34 between upper and lower surfaces 44, 46. Visualization openings 60 extend generally along longitudinal axis 21 of plate 22 and are generally positioned in the area adjacent the intervertebral disc space when plate 22 is attached to the vertebrae. In one embodiment, visualization openings 60 have an elongate hourglass-like configuration extending along virtually the entire length of the respective intermediate portions 34 and across a substantial portion of the width of the respective intermediate portions 34. However, it should be understood that other embodiments contemplate other sizes and shapes for visualization openings 60, such as, for example, a rectangular, elliptical or circular configurations, convexly curved side walls and convexly curved end walls, concavely curved side walls and concavely curved end walls, convexly curved end walls and concavely curved side walls, and combinations thereof. A plate without visualization openings is also contemplated.

In one embodiment, each of the connection portions 32 includes a pair of bone anchor openings 70, 71 positioned on opposite sides of axis 21 and each extending entirely through plate 22 between the upper and lower surfaces 44, 46. Bone anchors 24 are positionable through respective ones of the openings 70, 71 to anchor plate 22 to the spinal column. Other arrangements for bone anchor openings are also contemplated, including a single opening at one or more of each of the vertebral levels, more than two openings at one or more the vertebral levels, and/or one or more openings between the vertebral levels. Still other embodiments of stabilization system 10 contemplate a stabilization device 12 without bone anchor openings.

As further shown in FIGS. 6 and 7, each of the connection portions 32 of plate 22 includes an aperture 90 configured to receive a respective one of the retaining devices 26 therein, the details of which will be discussed below. Apertures 90 extend at least partially into plate 22 between upper and lower surfaces 44, 46, and are positioned generally along longitudinal axis 21 between a laterally adjacent pair of bone anchor openings 70, 71. Each of the apertures 90 includes a threaded portion 92 extending from lower surface 46 of plate 22 in communication with a countersunk portion extending from threaded portion 92 and opening onto upper surface 44. In one embodiment, the countersunk portion intersects and overlaps at least a portion of each of the bone anchor openings 70, 71, and receives retaining member 152 therein.

Although one configuration of the retaining device aperture 90 has been illustrated, it should be understood that other sizes and configurations are also contemplated. For example, aperture 90 may also be elongated to accept a retaining device longitudinally slidable or movable along or relative to plate 22. Aperture 90 can be configured to movably capture retaining device 26 in plate 22. Aperture 90 can include a portion 92 that is non-threaded, or be provided without a portion 92. Still other embodiments contemplate plate 22 without any aperture 90.

Referring to FIG. 6, shown therein is one embodiment of bone anchor 24 suitable for use with plate 22 of spinal stabilization system 10. Bone anchor 24 is a fixed-angle type bone screw. Bone anchor 24 includes a head portion 100 connected to a threaded shank portion 102 by an intermediate portion 104. Threaded shank portion 102 defines a number of threads 106 configured to engage vertebral bone and is sized to pass through the bone anchor openings 70, 71 defined through plate 22. Threads 106 are adapted to engage cortical and/or cancellous bone. In one embodiment, bone anchor 24 is configured as a self-tapping screw. In another embodiment, bone anchor 24 is configured as a self-drilling screw.

Intermediate portion 104 of bone anchor 24 has an outer diameter that is slightly smaller than the inner diameter of the cylindrical-shaped portion 80 of bone anchor openings 70, 71. Head portion 100 includes a spherical-shaped surface 110 that is substantially complementary to the spherically-shaped recess portion 82 defined by bone anchor openings 70, 71. Head portion 100 additionally includes a truncated or flattened upper surface 112 through which extends a tool receiving recess configured to receive a driving tool therein (not shown).

Referring to FIG. 7, shown therein is another embodiment of a bone anchor 25 suitable for use with spinal stabilization system 10 including plate 22. Bone anchor 25 is a variable-angle type bone screw. Variable-angle bone anchor 25 is configured similar to fixed-angle bone anchor 24, including a head portion 120 connected to a threaded shank portion 122 by an intermediate portion 124. Threaded shank portion 122 defines a number of threads 126 configured to engage vertebral bone. Like fixed-angle bone anchor 24, variable-angle bone anchor 25 may also be configured as a self-tapping or a self-drilling screw. However, unlike intermediate portion 104 of bone anchor 24, intermediate portion 124 of bone anchor 25 has an outer diameter that is significantly smaller than the inner diameter of the cylindrical-shaped portion 80 of bone anchor openings 70, 71 to permit angulation in openings 70, 71. Head portion 120 includes a spherical-shaped surface 130 that is substantially complementary to the spherical-shaped recess portion 82 defined by the bone anchor openings 70, 71 to facilitate variable angle placement and securement with plate 22. Head portion 120 also includes a truncated or flattened upper surface 132 through which extends a tool receiving recess configured to receive a driving tool therein (not shown).

In the illustrated embodiment, auxiliary element 14 includes retaining device 26 that includes first and second components engageable to or engaged with stabilization device 12. In the illustrated embodiment, a first component of auxiliary element 14 includes a fastener 150 and a second component includes a retaining member 152. Although a specific configuration of retaining device 26 has been illustrated and described, it should be understood that other configurations of retaining devices are also contemplated as discussed herein.

In FIG. 6 holding element 200 is placed through cannulation 172 of retaining device 26 and into engagement with vertebra 600 of the spinal column. Additional holding elements can be positioned in other retaining devices along plate 22 as needed to prevent plate 22 from twisting or rotating relative to the spinal column. Retaining device 26 is provisionally secured to plate 22 so that retaining element 152 can be moved proximally and/or side-to-side to facilitate insertion of bone anchors, such as bone anchors 24, into openings 70, 71. In FIG. 7, retaining device has been advanced into aperture 90 so that retaining element 152 contacts the heads of the bone anchors, such as the bone anchors 25. Holding element 200 can engage the head of fastener 150 and can be manipulated manually or with a tool engaged thereto to advance retaining device 26 to this engaged position relative to plate 22. Alternatively, holding element 200 can be removed and a tool used to secure retaining device 26 in the engaged position.

Figure 3:
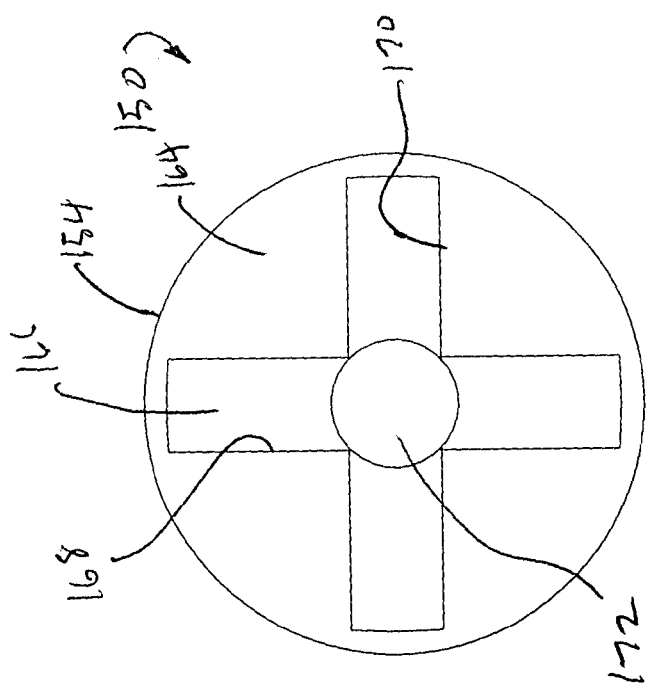
FIG. 3 is a left end view of the portion of the auxiliary element shown in FIG. 2.

As further shown in FIGS. 2 and 3, fastener 150 includes a head portion 154 and a threaded shank portion 156 extending therefrom. Threaded shank portion 156 defines a number of machine threads 158 configured to engage threaded portion 92 of aperture 90 defined by plate 22. Threaded shank portion 156 terminates in a relatively flat distal end 160. Head portion 154 includes an outwardly tapering conical surface 162. In one embodiment, conical surface 162 defines a taper angle of approximately 45 degrees. Head portion 154 further includes an upper surface 164 with a tool receiving portion 166 configured to receive a driving tool. As discussed further below, fastener 150 includes cannulation 172 extending therein and opening at least at the proximal end of fastener 150.

Cannulation 172 can include a constant cross-section along its length, or can be tapered, threaded, or enlarged at a distal end thereof for attachment of a holding element. Cannulation 172 can be used for attachment of a holding element, a barrier or blocking member, or other tool. Cannulation 172 can be, for example, partially or fully threaded or otherwise shaped for engagement with a tool to install or remove retaining device 26 should tool receiving portion 166 of fastener 150 become compromised or inaccessible.

In one embodiment, tool receiving portion 166 is a Phillips-type recess including a first recess portion 168 and a second recess portion 170. However, other types and shapes of tool receiving recesses are also contemplated, including hexagonal, starburst shaped, allen, single-slotted recesses, and multi-slotted recesses, for example. Other embodiments contemplate that tool receiving portion 166 extends proximally from head portion 154 to provide a post or member for engagement with a driving tool. Retaining member 152 has an outer surface substantially complementary to an outer surface of the head of the adjacent bone anchor 24, 25. Retaining member 152 can also include a central opening to receive fastener 150 therethrough.

Referring to FIGS. 4 and 5, there is shown one embodiment of a holding element 200. In the illustrated embodiment, holding element 200 includes distal portion 202 that is elongated for placement through cannulation 172 and into the spinal column. Other embodiments contemplate distal portion 202 of holding element 200 extends into the proximal opening of cannulation 172, and is attached to auxiliary element 14 therein via threads, an expansion fit, an interference fit, or other suitable attachment mechanism or structure.

In the illustrated embodiment, distal portion 202 includes a penetrating element 208 at the distal end of a shaft 210. Penetrating element 208 can be a sharpened tip, and shaft 210 includes a smooth surface profile. Other embodiments contemplate that shaft 210 includes threads, axial grooves, radial grooves, roughening, pits or other surface features to facilitate engagement and or insertion into the spinal column.

Proximal portion 204 includes a tool engaging portion 212 adjacent intermediate portion 206. A proximal shaft 214 extends proximally from tool engaging portion 212 to a recess 218. A proximal end portion 216 extends proximally from recess 218. Recess 218 can extend completely around proximal shaft 214, and facilitates engagement with a driving instrument, as discussed further below.

Intermediate portion 206 includes a frusto-conically tapered body portion 220 extending distally from tool engaging portion 212 to a distally oriented engagement surface 222. Engagement surface 222 can be configured to engage the tool receiving portion at the proximal end of fastener 150. In the illustrated embodiment, engagement surface 222 includes a first projection 224 and a second projection 226 configured to reside within correspondingly aligned recess portions 168, 170 of fastener 150.

Referring again to FIG. 6, shown therein is plate 22 attached to a vertebra 600 via fixed-angle bone anchors 24. In FIG. 7, plate 22 is attached to vertebra 600 with variable angle anchors 25. Initially, plate 22 is positioned along the spinal column so as to extend between at least two vertebrae, with lower surface 46 positioned in abutment against an outer surface of vertebra 600. At least one holding element 200 is placed through cannulation 172 of fastener 150. It is contemplated that two holding elements 200 positioned through various ones of the fasteners 150 spaced axially along plate 22 will prevent plate 22 from twisting or rotating on the spinal column. Connection portion 32 of plate 22 is then secured to vertebra 600 by passing threaded portions 102 of bone anchors 24, 25 through respective ones of the bone anchor openings 70, 71 and driving threaded portions 102 into vertebral bone. Conical portions 84 of bone anchor openings 70, 71 adjacent upper Surface 44 serve to facilitate insertion of bone anchors 24 into bone anchor openings 70, 71 and/or to aid in positioning and orientation of screw guides, drill guides, drills or other instrumentation (not shown) relative to plate 22. The spherical-shaped recess portions 82 act as a countersink for head portions of bone anchors 24, 25, thereby allowing a significant portion of anchor heads to be positioned beneath upper surface 44 of plate 22 to minimize the overall height or profile of the assembly in situ.

Once the desired bone anchors 24, 25 are fully driven into vertebra 600 and plate 22 is securely attached to vertebra 600, retaining devices 26 are positioned to prevent bone anchors 24, 25 from loosening and backing out of plate 22. Threaded shank portion 156 of fastener 150 is threaded distally into threaded portion 92 of aperture 90 by way of rotating holding element 200 engaged with tool receiving portion 166. Alternatively, holding element 200 can be removed and a driver (not shown) engaged within tool receiving portion 166 to drive fastener 150 distally into threaded portion 92. In any event, fastener 150 is driven through threaded portion 92 of aperture 90 until lower conical surface 162 of fastener head 154 engages retaining member 152. Retaining member 152 in turn engages against the adjacent surface of the heads of anchors 24, 25 to prevent anchors 24, 25 from loosening and backing out of plate 22.

Referring to FIG. 1, plate 22 attached to the spinal column so that intermediate portions 34 and visualization openings 60 are positioned approximately adjacent respective intervertebral disc spaces 606, 607. Visualization openings 60 and the reduced lateral profile of the intermediate portions 34 of plate 22 provide the capability to visualize the intervertebral disc spaces 606, 607 and/or spinal implants 660 or other devices or instruments positioned within the intervertebral disc spaces 606, 607. More specifically, these features provide for direct visualization of implants 660 disposed within the intervertebral disc spaces 606, 607, the relationship between plate 22 and implants 660, and/or the interface between implants 660 and the vertebral endplates. Such implants 660 may include, for example, bone grafts, artificial fusion devices, artificial discs, or any other type of interbody device that is insertable within the intervertebral disc space. Further examples of such implants include bone dowels, push-in type cages, screw-in type cages, tapered cages, cages filled with bone graft and/or graft substitute material or other types of devices suitable for fusion applications, external or internal stabilization of a segment of the spinal column or other types of bony segments.

In FIG. 1 a single implant 660 is centrally disposed within each intervertebral disc space 606, 607. Visualization openings 60 can provide means for direct visualization of implants 660 in relation to the intervertebral disc spaces 606, 607. However, in another embodiment, a pair of implants 660 may be inserted bilaterally within each intervertebral disc space 606, 607. In still another embodiment, one or more auxiliary elements 14 are aligned with one or more of the disc spaces 606, 607, and holding element 200 is positioned through the auxiliary element to secure stabilization device 12 to an implant, device, soft tissue or other structure associated with the disc space. In another embodiment, one or more auxiliary elements 14 are aligned with a device positioned between vertebrae, such as a disc space device or corpectomy device, and one or more holding elements 200 are positioned through corresponding ones of the auxiliary elements 14 to secure stabilization device 12 to the device between vertebrae.

It is further contemplated that tools can be provided to facilitation placement, manipulation, and/or removal of holding element 200 relative to auxiliary element 14. For example, FIGS. 8-15 show a driving instrument 300 useable with holding element 200 for such purposes. Driving instrument 300 includes a handle portion 302, a first member 320 and a second member 350. First and second members 320, 350 extend distally from handle portion 302, and engage holding element 200 for remote manipulation through handle portion 302.

Handle portion 302 includes a body 312 with a number of axial grooves 314 formed therein to facilitate manual gripping. A proximal end of body 312 includes a cap 304 rotatably captured about a proximal extension 306. Proximal extension 306 includes a raised lip 307 extending thereabout to secure cap 304 thereon. The freely rotating cap 304 facilitates manipulation of driving instrument 300 with a single hand of the user since a palm of the use can rest on cap 304 and handle portion 302 can be rotated with the user's fingers.

Body 312 further includes a distal end 308 with a first outer opening portion 310 extending proximally from distal end 308. A second inner opening portion 316 extends proximally further into body 312 from outer opening portion 310. An endwall 311 extends between outer opening portion 310 and inner opening portion 316.

First member 320 includes an elongated shaft 322 extending between a distal end 324 and a proximal end 326. A ring 328 extends about shaft 322 adjacent proximal end 326. As shown in FIGS. 10 and 15, shaft 322 includes a proximal end passage portion 330 and, as shown in FIG. 14, a distal end passage portion 332. An intermediate passage portion 334 extends therebetween. A spring 338 is positioned within proximal end portion 326 and is biased between an endwall 311 at the junction of opening portions 310, 316 of handle portion 302 and an endwall 331 at the junction of passage portions 330, 334 of first member 320.

As shown in FIGS. 11-13, second member 350 includes a shaft portion 352 sized for receipt in intermediate passage 334 of first member 320. A distal head portion 354 at the distal end of shaft 352 includes a distal end 355 that includes holding element engaging portion 356. In the illustrated embodiment, holding element engaging portion 356 is a recess formed internally into head portion 354. Head portion 354 is frusto-conical and tapers outwardly from distal end 355 to a proximally facing shoulder 357. A number of openings 360 extend through shaft 352 in a distal portion thereof adjacent to and spaced proximally from shoulder 357. Coupling members 370 are movable in respective ones of the openings 360 and can project into a central passage 358 of shaft 352. Coupling members 370 can be spherical or of other suitable form to provide axial securement of proximal portion 204 of holding element 200 with driving instrument 300.

The proximal end 364 of shaft portion 352 includes a first reduced diameter portion 362 about which spring 338 is positioned. A second reduced diameter portion 366 extends proximally from first portion 362, and includes a diameter smaller than first reduced diameter portion 362. Second reduced diameter portion 366 is engaged in inner opening portion 316 of handle portion 302 to secure second member 350 thereto.

When assembled, second member 350 is secured to handle portion 302. First member 320 is positioned about second member 350, and biased distally via spring 338 into contact with proximally facing shoulder 357 of second member 350. In this position, as shown in FIG. 14, intermediate passage portion 334 is positioned over openings 360 to bias a coupling device including one or more coupling members 370 into the corresponding openings 360. In this coupled position, coupling members 370 project into central passage 358 of second member 350. Ring portion 328 of first member 320 can be grasped to manually pull first member 320 proximally relative to second member 350 and handle portion 302 so that proximal end 326 is moved proximally into first outer opening portion 310. This movement aligns the larger distal passage portion 332 of first member 320 with opening 360, allowing coupling member 370 to move freely outwardly in openings 360 to a release position so as to not obstruct central passage 358. When first member 320 is released, spring 338 returns it toward its position shown in FIG. 14 into contact with proximally facing shoulder 357.

Figure 16:
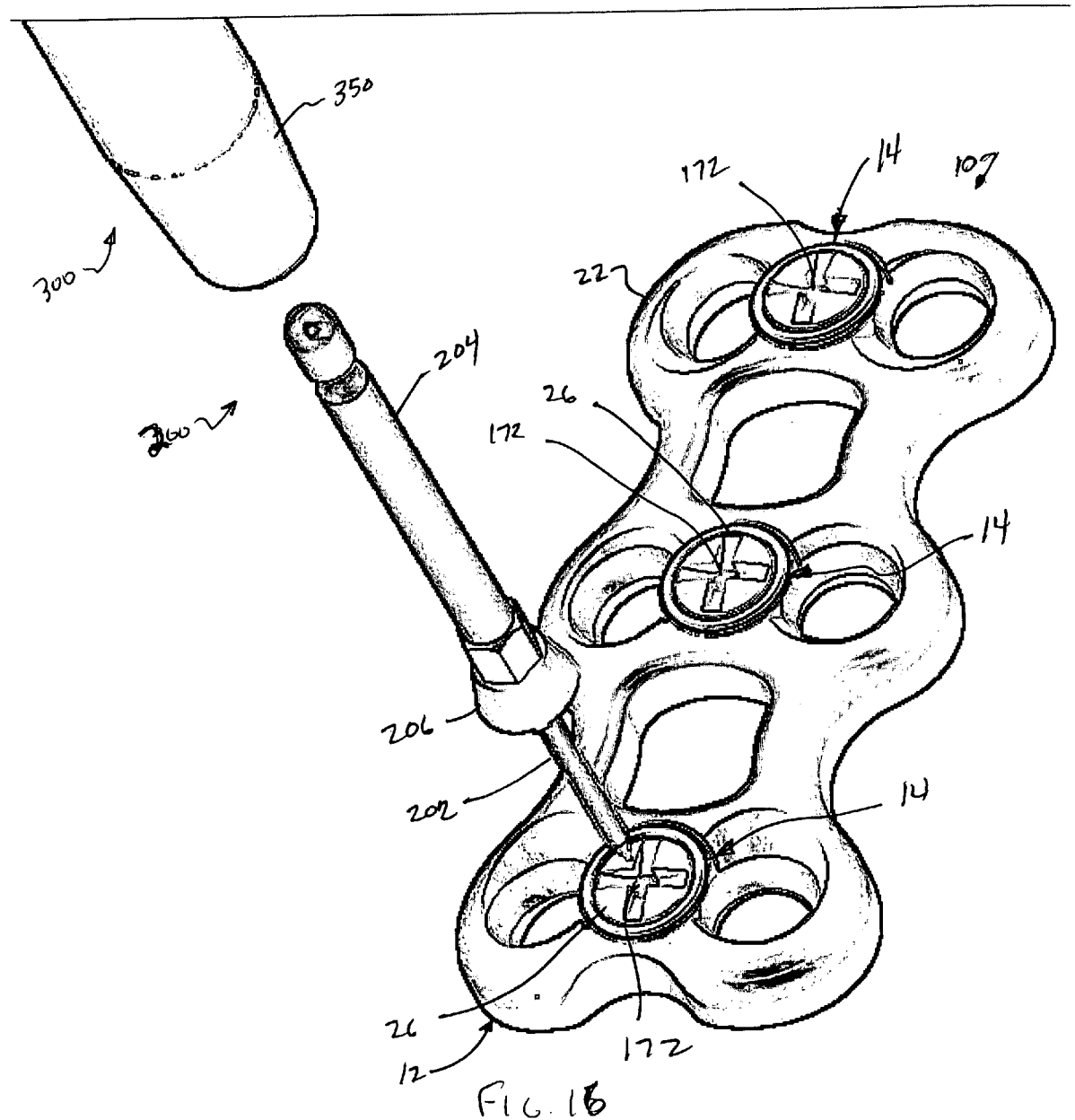
FIG. 16 is a perspective view showing the stabilization system of FIG. 1 and the holding element of FIG. 4 aligned with a cannulated auxiliary element of the stabilization system and disengaged from the driving instrument of FIG. 8.
Figure 17:
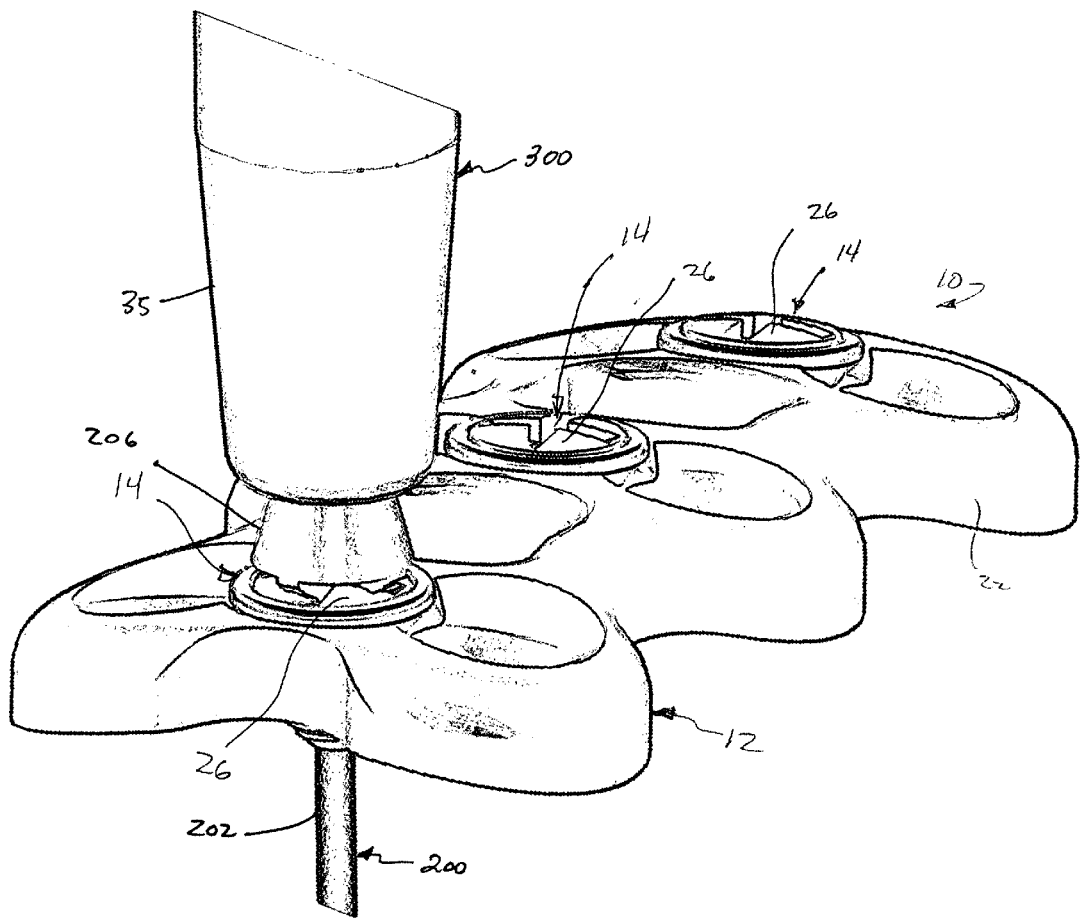
FIG. 17 is a perspective view showing the stabilization system of FIG. 1 and the holding element of FIG. 4 positioned through the cannulated auxiliary element of the stabilization system and engaged with the driving instrument of FIG. 8.

FIGS. 16 and 17 show driving instrument 300 in use with holding element 200 and stabilization system 10. Proximal portion 204 of holding element 200 is inserted into the distally opening holding element engaging portion 356 at distal end 355 of second member 350. First member 320 is retracted proximally to allow coupling members 370 to move freely as proximal end 204 is inserted thereby. Holding element engaging portion 356 engages tool engaging portion 212 of holding element 200 with recess 218 aligned with coupling members 370. First member 320 is then released and coupling members 370 are pushed into holes 360 and into engagement with recess 218 of holding element 200, axially securing holding element 200 to driving instrument 300.

Holding element 200 can then be inserted through cannulation 172 of auxiliary element 14 until the distally oriented engagement surface 222 engages auxiliary element 14. When inserted into the spinal column structure underlying auxiliary device 12, holding element 200 can be employed for temporary fixation and/or alignment of stabilization device 12 on the spinal column. One or more additional holding elements 200 are positioned through corresponding cannulations 172 of additional auxiliary elements 14. Repositioning of stabilization device 12 can be accomplished by withdrawing one of the holding elements 200 from the spinal column, repositioning stabilization device 12 on the spinal column, and re-securing stabilization device 12 at the revised location. One end of stabilization device 12 can remain secured to the spinal column with a second holding element 200 as the plate is repositioned. This repositioning procedure can be repeated by removing the holding element 200 at the location necessary to achieve the desired alignment.

Holding element 200 can be used to maintain alignment of or positioning of auxiliary element 14 relative to plate 22. For example, the engagement surface 222 can engage auxiliary element 14 to prevent it from moving or twisting during the procedure to obstruct access to the anchor openings. After inserting anchors into the openings of stabilization device 12, or the completion of other procedures, driving instrument 300 can be manipulated to drive the engaged auxiliary elements 14 with holding element 200 to a second position or orientation relative to stabilization device 12. For example, an auxiliary element 14 with a first component such as locking fastener 150 can be manipulated with holding element 200 through driving instrument 300 to advance locking fastener 150 distally into aperture 90 of plate 22. When retaining member 152 is seated against the anchors or against plate 22, retaining member 152 is positioned to block the inserted bone anchors and resist or prevent their backing out of the plate openings. Driving instrument 300 can then be used to apply a proximally and axially directed force to holding element 200 to withdraw holding element 200 from the cannulation 172 of auxiliary element 14.

It should be understood that stabilization system 10 can be used in conjunction with fusion-type implants that promote fusion between adjacent pairs of vertebrae and/or spacer-type implants that serve to maintain a spacing between adjacent pairs of vertebrae in intradiscal and corpectomy procedures. In applications involving fusion type implants, stabilization system 10 can include plate 22 to provide temporary stabilization during the fusion process. Following fusion of the adjacent vertebrae, plate 22 may be removed from the patient, may be maintained within the patient, or may be formed of a resorbable material that is resorbed into the patient over a period of time.

In one embodiment, the instrumentation used to position and attach the plate to the vertebrae may be secured to the cannulated auxiliary elements 14. Such instrumentation may include, for example, templates, plate holders, bone screw guides, drivers, or other instruments or devices typically associated with the placement and attachment of a plate or any stabilization device to one or more vertebrae.

Figure 19:
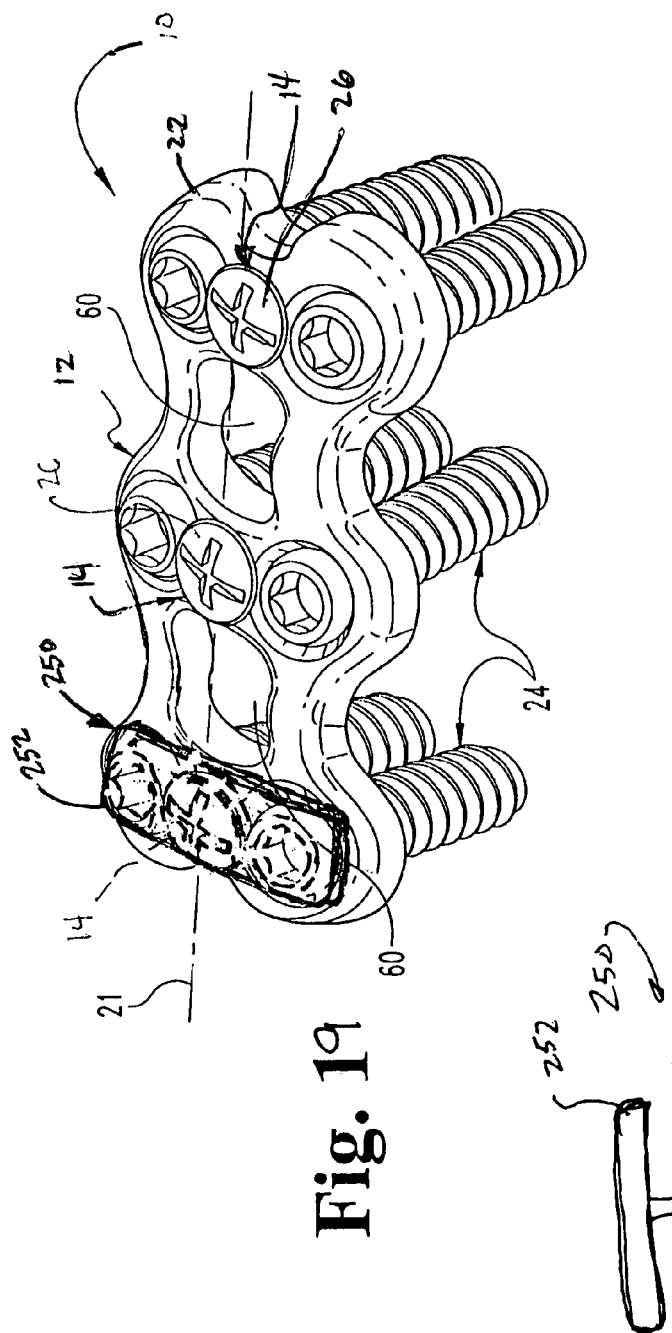
FIG. 19 is a perspective view of a stabilization system with the blocking member of FIG. 18 secured to an auxiliary element.
Figure 18:
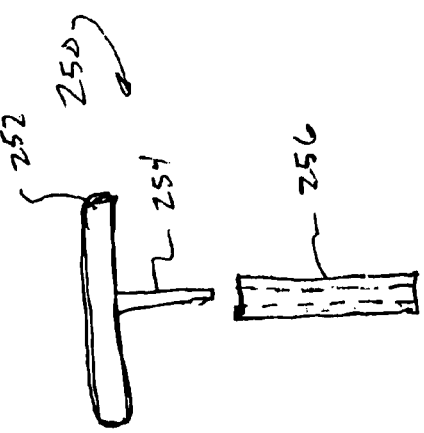
FIG. 18 is an elevation view of a blocking member.

In FIG. 18 there is shown a blocking member 250. Blocking member 250 includes a body portion 252 and an engagement portion 254 extending from body portion 252. Engagement portion 254 is attachable to cannulation 172 of auxiliary element 14 with body portion 252 extending over and substantially covering anchors 24 and auxiliary element 14, as shown in FIG. 19. Engagement portion 254 can be coupled directly to auxiliary element 14 in cannulation 172.

In another embodiment, a retention device 256 such as a sleeve is positioned in cannulation 172 and engaged to auxiliary element 14 and/or the underlying structure of the spinal column. Blocking member 250 can then be engaged to the retention device 256 for attachment to auxiliary element 14. The retention device 256 can include an outer surface that is tapered, threaded or otherwise configured for engagement with auxiliary element 14 in cannulation 172. The retention device 256 can be provided with a length sufficient to extend the retention device 256 distally beyond the cannulation for engagement with the underlying structure of the spinal column. Engagement portion 254 of blocking member 250 can then be engaged, by threads, friction or other suitable means, in an internal lumen of retention device 256 to facilitate later removal in case of revision surgery.

Blocking member 250, when employed with retaining device 26 as shown, provides secondary blocking of anchors 24 to resist anchor back out from the plate openings. Body portion 252 of blocking member 250 can substantially cover the anchors to provide visual confirmation that the bone anchors are completely covered and unable to back out into the surrounding tissue post-implantation. Additionally or alternatively, blocking member 252 can function as a barrier to prevent tissue growth and/or migration into the tool engagement openings of auxiliary element 14 and the adjacent bone anchors 24, facilitating removal in the case of revision surgery. In still a further embodiment, cannulation 172 can receive a substance, such as a reabsorbable material or polyetheretherketone (PEEK) to seal anchors 24 and/or auxiliary element 14 from bioactivity.

Figure 20:
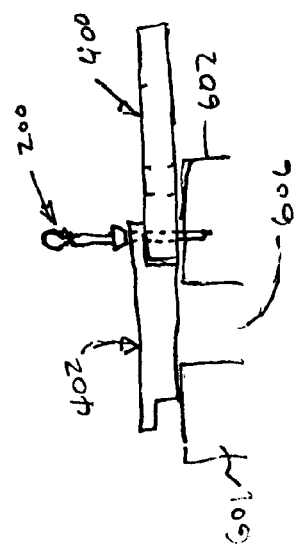
FIG. 20 is an elevation view of a multi-component stabilization system along the spinal column.

In still another application, holding element 200 can be employed in the temporary linkage or permanent linkage of multiple stabilization devices that comprise a stabilization system positionable along the spinal column, such as shown in FIG. 20. In FIG. 20, a first stabilization device 400 is positioned along the spinal column, such as along vertebra 602. A second stabilization device 402 is positioned to at least partially overlap first stabilization device 400. Holding element 200 is placed through aligned cannulations of the stabilization devices 400, 402, or through aligned cannulations of auxiliary elements associated with one or more of the stabilization devices 400, 402, to temporarily secure stabilization devices 400, 402 in a desired position and/or orientation along the spinal column. It is contemplated that multiple stabilization devices 400, 402 can be provided to increase a length of a stabilization system, or to increase the strength of a stabilization system by allowing placement of multiple stabilization devices adjacent one another in overlapping or side-by-side positioning along the spinal column.

Figure 21:
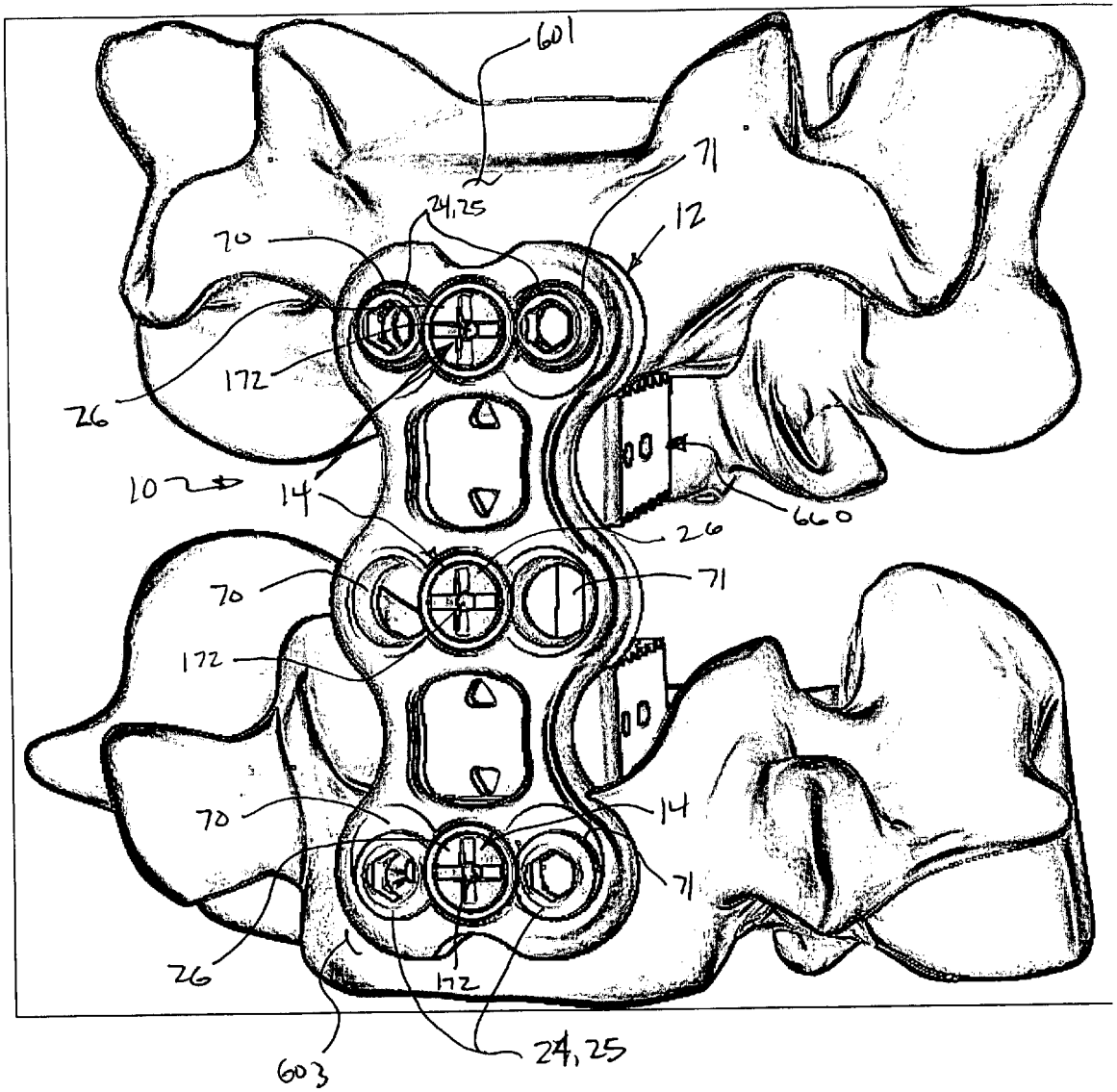
FIG. 21 is an elevation view of a stabilization system securable to a device positioned in the spinal column with a holding element.
Figure 22:
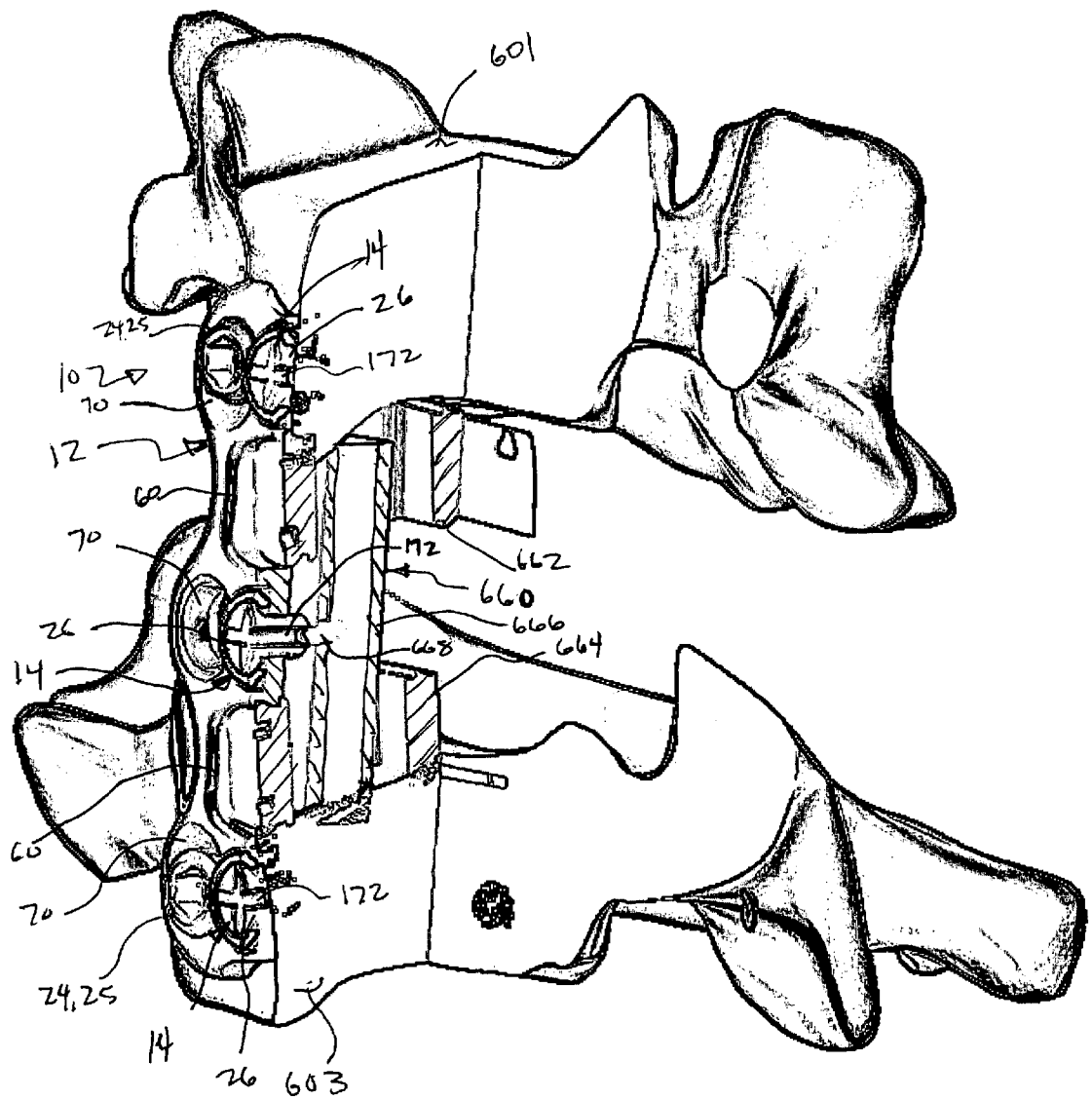
FIG. 22 is an elevation view of the stabilization system and device of FIG. 21 in partial section.
Figure 23:
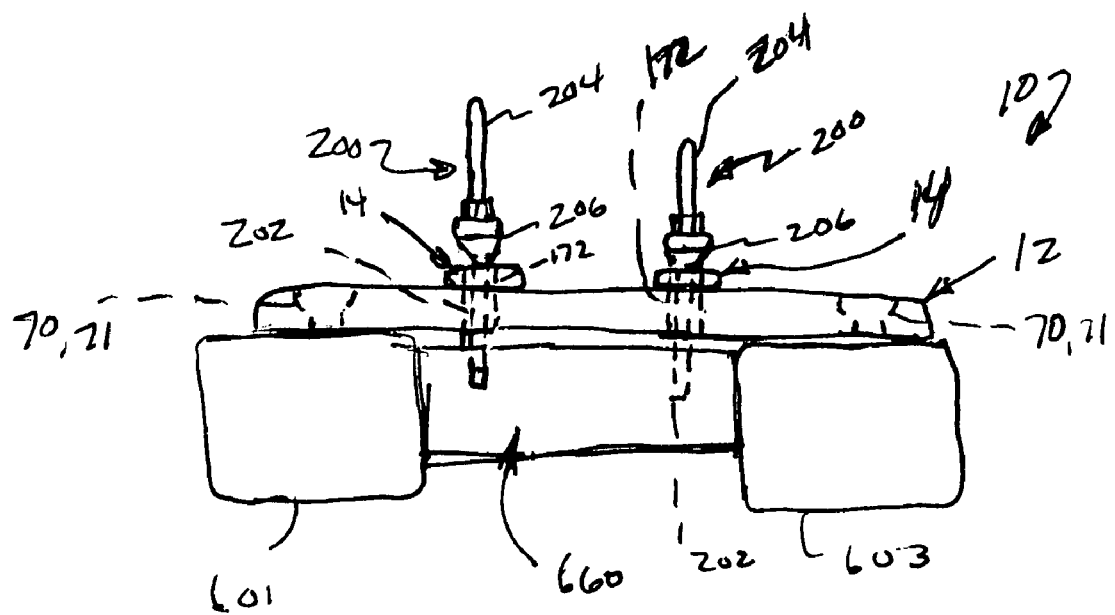
FIG. 23 is another embodiment elevation view of a stabilization system securable to a device positioned in the spinal column with a holding element.

FIGS. 21-23 provide other examples of applications for attaching stabilization system 10 to the spinal column with holding elements 200. An implant 660 is positioned between vertebrae 601, 603. In the illustrated embodiment, the vertebra between vertebrae 601, 603 has been removed, and implant 660 is a corpectomy device. Other implant types are contemplated, including disc space devices, as discussed herein. In the illustrated embodiment of FIGS. 21 and 22, implant 660 includes an upper member 662 and a lower member 664. An intermediate member 666 extends between upper and lower members 662, 664 and provides the desired spacing therebetween to support vertebrae 601, 603. In FIG. 23, implant 660 is illustrated as a unitary strut that extends between vertebrae 601, 603.

Stabilization device 12 is positioned along the spinal column so that it can be anchored to vertebrae 601, 603 by, for example, bone anchors 24, 25 positioned through anchor openings 70, 71. At least one auxiliary element 14 is aligned with implant 660, and includes cannulation 172 to receive holding element 200 therethrough. It is further contemplated that more than one cannulated auxiliary element 14 can be aligned with implant 660, such as shown in FIG. 23. Cannulated auxiliary elements 14 can also be aligned with one or both of vertebrae 601, 603. It is also contemplated that one or more of the auxiliary elements 14 can be provided without a cannulation.

Intermediate member 666 can include a receptacle 668 to receive the distal portion 202 of holding element 200. Receptacle 668 can be adapted to engage the distal portion 202 of holding element 200 by friction, threaded engagement, or with any other suitable engaging relationship. Multiple receptacles 668 can be provided along implant 660 to facilitate alignment of cannulation 172 with the implant. It is also contemplated that distal portion 202 of holding element 200 can penetrate into the body of implant 660, eliminating the need to align the cannulation of auxiliary element 14 with a hole in the implant. It is further contemplated that implant 660 can include a projection or other structure extending therefrom adapted to receive and engage distal portion 202 of holding element 200.

Holding elements 200 can provide temporary securement of stabilization device 12 by securing stabilization device 12 to implant 660 and/or vertebrae 601, 603. In FIGS. 21 and 22, the centrally located auxiliary element 14 is aligned with intermediate member 666. Other embodiments contemplate that one or more auxiliary elements 14 can be aligned with one or both of the upper and lower members 662, 664 in addition to or in lieu of intermediate member 666. With stabilization device 12 positioned along the spinal column, a holding element 200 can be positioned through the corresponding auxiliary element 14 aligned with implant 660, and engaged with implant 660 to secure stabilization device thereto. A second holding element 200 can be positioned through the cannulated auxiliary element aligned with one of the vertebrae 601, 603, providing additional securement of stabilization device 12 to the spinal column during the subsequent anchoring steps.

In the embodiment of FIG. 23, for example, two holding elements 200 are used to secure stabilization device 12 to implant 660. Bone anchors can then be positioned to anchor stabilization device 12 to vertebrae 601, 603 while its positioning on the spinal column is maintained with holding elements 200 engaged to implant 660. Holding elements 200 can be removed after stabilization device 12 is anchored to the spinal column, or remain in situ post-operatively.

Various techniques, devices and instrumentation are provided to position stabilization systems in relation to the spinal column. These techniques, devices and instrumentation are designed and/or configured in such a manner as to minimize interference with placement, visualization and manipulation of implants and surgical instruments in the surgical space during the surgery and post-implantation in case revision of the stabilization system is desired.

While the invention has been illustrated and described in detail in the drawings and foregoing description, the same is to be considered as illustrative and not restrictive in character, and that all changes and modifications that come within the spirit of the invention are desired to be protected.

The invention claimed is:

1. A spinal stabilization system, comprising:
a stabilization device positionable along a spinal column, said stabilization device including at least one auxiliary element mounted thereto, said at least one auxiliary element including a cannulation extending at least partially therethrough between a proximal opening of said auxiliary element oriented away from the spinal column and a distal opening of said auxiliary element oriented toward the spinal column when said stabilization device is positioned along the spinal column; and
a holding element including a distal portion and a proximal portion, said distal portion including an elongated shaft extending from said proximal portion to a distal end, wherein with said at least one auxiliary element mounted to said stabilization device said distal end of said distal portion is configured for placement into said proximal opening and through said distal opening of said cannulation to advance said shaft through said proximal opening to releasably engage a distal end of said proximal portion with said auxiliary element in an interfitting relationship and position said distal end of said shaft distally of said distal opening of said auxiliary element to enter into bone and engage the spinal column to maintain a positioning of said stabilization device along the spinal column and said distal end of said proximal portion preventing said auxiliary element from moving relative to said stabilization member, wherein when said holding element is engaged to said auxiliary element with said distal portion of said holding element extending distally from said auxiliary element and into bone of the spinal column, rotation of said proximal and distal portions of said holding element rotates said auxiliary element relative to said stabilization device.

2. The system of claim 1, wherein said stabilization device comprises an elongated plate including a number of bone anchor openings extending therethrough.

3. The system of claim 2, wherein said auxiliary element includes a retaining device engaged to said plate at a location offset from said number of bone anchor openings and is positionable relative to said elongated plate to at least partially overlap at least one of said bone anchor openings.

4. The system of claim 3, wherein said retaining device includes a fastener with a proximal head and a threaded stem extending distally from said proximal head, said threaded stem threadingly engages plate and said cannulation extends along a central axis of said fastener and with said distal opening at a distal end of said stem and said proximal opening at a proximal end of said head.

5. The system of claim 4, wherein said retaining device includes a retaining member including a central aperture for receiving said fastener.

6. The system of claim 4, wherein said elongated plate includes an aperture extending therethrough and said fastener is engageable with said aperture.

7. The system of claim 1, wherein said auxiliary element is movable relative to said stabilization device.

8. The system of claim 7, wherein said holding element engages said auxiliary element and is movable to manipulate said auxiliary device to a desired position relative to said stabilization device.

9. The system of claim 1, wherein said distal end of said proximal portion of said holding element includes a distally oriented engagement surface for engaging said auxiliary element, said distally oriented engagement surface projecting outwardly around said distal portion of said holding element and including at least one projection for receipt in a recess in said auxiliary element in said interfitting relationship.

10. The system of claim 9, wherein said holding element includes an intermediate portion between said distal portion and said proximal portion, said proximal portion including a shaft and a first driving tool engaging portion adjacent said intermediate portion that projects outwardly from said shaft, said intermediate portion further including a tapered body portion sloping from said distally oriented engagement surface to said first driving tool engaging portion.

11. The system of claim 10, wherein said proximal portion of said holding element includes a second driving tool engaging portion adjacent a proximal end of said shaft of said proximal portion that includes a recess in an outer surface of said shaft.

12. The system of claim 1, wherein said shaft includes a smooth surface profile extending proximally from said distal end of said shaft.

13. The system of claim 1, further comprising a device positionable between vertebrae of a spinal column and wherein said stabilization device is positionable along the vertebrae.

14. The system of claim 13, wherein:
said cannulation extends completely through said auxiliary element; and
said distal portion of said holding element extends through said auxiliary element and is engageable with said device when said stabilization device is positioned along the spinal column.

15. The system of claim 13, wherein said device is a corpectomy implant and said stabilization device is an elongated plate.

16. The system of claim 1, further comprising an instrument engageable to said proximal portion of said holding element.

17. The system of claim 16, wherein said proximal portion of said holding element includes a first instrument engaging portion adapted to deliver a rotational force from said instrument to said holding element and a second instrument engaging portion to simultaneously axially secure said instrument to said holding element.

18. A spinal stabilization system, comprising:
a stabilization device positionable along a spinal column and including an auxiliary element associated therewith and movable relative thereto, said auxiliary element including a cannulation extending between a proximal opening and a distal opening of said auxiliary element, said auxiliary element further including a proximal engagement surface; and
a holding element including a distal portion positionable in said cannulation of said auxiliary element and configured to enter into bone of the spinal column, a proximal portion extending proximally from said distal portion, and an intermediate portion therebetween, wherein said distal portion includes an elongated shaft extending from said intermediate portion to a distal end, wherein with said at least one auxiliary element mounted to said stabilization device said distal end of said distal portion is configured for placement into said proximal opening and through said distal opening of said cannulation to advance said shaft through said proximal opening to releasably engage a distally oriented engagement surface of said intermediate portion with said proximal engagement surface of said auxiliary element in an interfitting relationship and position said distal end of said shaft distally of said distal opening of said auxiliary element to enter into bone and engage the spinal column to maintain a positioning of said stabilization device along the spinal column, wherein said distal and intermediate portions of said holding element being movable when said distally oriented engagement surface is interfitted with said proximal engagement surface and said distal portion is entered into bone of the spinal column to move said auxiliary element in a desired position relative to said stabilization device.

19. The system of claim 18, wherein said stabilization device comprises an elongated plate including a number of bone anchor openings extending therethrough.

20. The system of claim 19, wherein said auxiliary element includes a retaining device positionable relative to said elongated plate to at least partially overlap at least one of said bone anchor openings.

21. The system of claim 18, wherein said proximal portion of said holding element includes a first driving tool engaging portion proximally of and adjacent to said intermediate portion and a shaft extending proximally from said first driving tool engaging portion, said first driving tool engaging portion extending outwardly from said shaft, said intermediate portion further including a tapered body sloping from said distally oriented engagement surface to said first driving tool engaging portion, said proximal portion further including a second driving tool engaging portion on said shaft spaced from said first driving tool engaging portion and adjacent to a proximal end of said proximal portion.

22. The system of claim 21, wherein said second driving tool engaging portion includes a recess in an outer surface of said shaft.

23. The system of claim 18, wherein said proximal portion of said holding element includes a first instrument engaging portion adapted to deliver a rotational force from an instrument to said holding element and a second instrument engaging portion adapted to axially secure the instrument to said holding element.

24. A spinal stabilization, comprising:
a stabilization device including a cannulation and an auxiliary element; and
a holding element including a distal portion with an elongated first shaft extending to a sharp distal tip positionable in said cannulation of said stabilization device, a proximal portion extending proximally from said distal portion, and an intermediate portion therebetween that projects outwardly from said proximal portion and said distal portion, said intermediate portion including at least one projection extending distally therefrom and outwardly from said distal portion adapted to engage said auxiliary element of said stabilization device and deliver a rotational force thereto, wherein said proximal portion of said holding element includes a second shaft and a first instrument engaging portion projecting outwardly from said second shaft that is adapted to receive a rotational force delivered to said holding element that rotates said proximal portion and said distal portion in said cannulation and a second instrument engaging portion spaced from said first instrument engaging portion adapted to receive an axial force delivered to said holding element, wherein with said auxiliary element mounted to said stabilization device said distal tip of said first shaft is configured for placement into a proximal opening of said cannulation and through a distal opening of said cannulation to advance said first shaft through said proximal opening to releasably engage said at least one projection of said intermediate portion with said auxiliary element in an interfitting relationship and position said distal tip of said first shaft distally of said distal opening of said cannulation to enter into bone and engage the spinal column to maintain a positioning of said stabilization device along the spinal column with said at least one projection of said intermediate portion preventing said auxiliary element from moving relative to said stabilization device.

25. The device of claim 24, wherein said intermediate portion includes a distally oriented engagement surface projecting outwardly from said distal portion, said distally oriented engagement surface including said at least one projection extending distally therefrom.

26. The device of claim 25, wherein said sharp distal tip is located at a distal end of said first shaft and said first shaft includes a smooth surface profile extending proximally from said distal tip.

27. The device of claim 26, wherein said intermediate portion includes a frusto-conical body that tapers from said distally oriented engagement surface to said first instrument engaging portion.

28. The device of claim 27, wherein said first instrument engaging portion includes a head proximally of and adjacent to said intermediate portion that is shaped to receive a tool thereover and said second instrument engaging portion is a recess adjacent to a proximal end of said shaft of said proximal portion.

* * * * *

UNITED STATES PATENT AND TRADEMARK OFFICE
CERTIFICATE OF CORRECTION

PATENT NO. : 7,625,375 B2 Page 1 of 1
APPLICATION NO. : 10/635319
DATED : December 1, 2009
INVENTOR(S) : Garden et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1401 days.

Signed and Sealed this

Twenty-sixth Day of October, 2010

David J. Kappos
*Director of the United States Patent and Trademark Office*